United States Patent

Hayes et al.

[11] Patent Number: 5,471,063
[45] Date of Patent: Nov. 28, 1995

[54] FLUID DISINFECTION SYSTEM

[75] Inventors: Stewart J. Hayes; Richard Pearcey; Philip T. White, all of London, Canada

[73] Assignee: Trojan Technologies, Inc., Canada

[21] Appl. No.: 181,107

[22] Filed: Jan. 13, 1994

[51] Int. Cl.[6] .................................................. C02F 1/32
[52] U.S. Cl. .................. 250/436; 250/455.11; 267/166; 210/748
[58] Field of Search ........................ 250/436, 455.11; 267/166, 166.1, 167, 180; 210/748

[56] References Cited

U.S. PATENT DOCUMENTS

| | | | |
|---|---|---|---|
| 2,413,704 | 12/1944 | Glatthar et al. | 250/42 |
| 2,670,439 | 2/1954 | Darney | 250/43 |
| 3,140,054 | 4/1963 | Oharenko | 240/2.18 |
| 3,182,191 | 5/1965 | McFarland et al. | 250/43 |
| 3,182,193 | 5/1965 | Ellner et al. | 250/43.5 |
| 3,456,107 | 7/1969 | Robertson | 250/43 |
| 3,462,597 | 8/1969 | Young | 250/43 |
| 3,622,832 | 11/1971 | Schlessel | 313/318 |
| 3,637,342 | 1/1972 | Veloz | 250/43 |
| 3,837,800 | 9/1974 | Wood | 210/64 |
| 3,924,139 | 12/1975 | Hirose et al. | 250/527 |
| 3,948,772 | 4/1976 | Ellner | 210/96 |
| 4,103,167 | 7/1978 | Ellner | 250/432 |
| 4,204,956 | 5/1980 | Flatow | 210/87 |
| 4,255,663 | 3/1981 | Lewis | 250/436 |
| 4,296,328 | 10/1981 | Regan | 250/436 |
| 4,367,410 | 1/1983 | Wood | 250/431 |
| 4,400,270 | 8/1983 | Hillman | 210/103 |
| 4,435,744 | 3/1984 | Russo | 362/219 |
| 4,471,225 | 9/1984 | Hillman | 250/436 |

(List continued on next page.)

FOREIGN PATENT DOCUMENTS

| | | |
|---|---|---|
| 421296 | 2/1911 | France . |
| 14626 | 1/1912 | France . |
| 434069 | 1/1912 | France . |
| 855521 | 11/1952 | Germany . |
| 2213658 | 10/1973 | Germany . |
| 3441535 | 6/1986 | Germany .......................... C02F 1/32 |
| 4102822 | 8/1992 | Germany .......................... F21S 3/02 |
| 56-118732 | 9/1981 | Japan ............................... B01J 19/12 |
| 56-118783 | 9/1981 | Japan ............................... C02F 1/32 |
| 1315688 | 6/1987 | U.S.S.R. ............................. 267/166.1 |
| 2141870 | 1/1985 | United Kingdom ........... H01J 61/02 |
| 2174197 | 10/1986 | United Kingdom ............. G01J 1/04 |

OTHER PUBLICATIONS

Die Katadyn UV–Verfahrer zur Keimreduktior im Abwassen Office National De La Propriete Industrielle, 1st addition, Au Brevet D'invention.

Sketch of UVPS System Allegedly Installed In Lebanon, Mo. WWTP Jul. 1988.

Primary Examiner—Jack I. Berman
Assistant Examiner—James Beyer
Attorney, Agent, or Firm—Fitzpatrick, Cella, Harper & Scinto

[57] ABSTRACT

A fluid disinfection unit comprising a fluid treatment housing, an electrical supply module and electrical connection means connecting the fluid treatment housing and the electrical supply module;

the fluid treatment housing comprising a fluid inlet and a fluid outlet in communication with a reaction chamber, an ultraviolet radiation lamp disposed in the reaction chamber and having a first electrical connection receiving means at a first end thereof and a second end thereof being closed, the second end of the ultraviolet radiation lamp being received and held in place by fixture means;

the electrical supply module comprising ballast means and a second electrical connection receiving means; and the electrical connection means comprising lamp receptacle connector means at one end thereof for removable connection to the ultraviolet radiation lamp and electrical connection receiving means for connection to the electrical supply module.

20 Claims, 5 Drawing Sheets

U.S. PATENT DOCUMENTS

| | | | |
|---|---|---|---|
| 4,482,809 | 11/1984 | Maarschalkerweerd | 250/436 |
| 4,490,777 | 12/1984 | Tanner et al. | 362/221 |
| 4,535,247 | 8/1985 | Kurtz | 250/436 |
| 4,591,958 | 5/1986 | Lamboo | 362/219 |
| 4,596,935 | 6/1986 | Lumpp | 250/495.1 |
| 4,661,890 | 4/1987 | Watanabe et al. | 362/217 |
| 4,700,101 | 10/1987 | Ellner et al. | 313/1 |
| 4,752,401 | 6/1988 | Bodenstein | 250/436 |
| 4,755,292 | 7/1988 | Merriam | 210/192 |
| 4,757,205 | 7/1988 | Latel et al. | 250/435 |
| 4,767,932 | 8/1988 | Ellner | 250/435 |
| 5,116,582 | 5/1992 | Cooper et al. | 422/186.3 |
| 5,266,215 | 11/1993 | Engelhard | 250/436 |

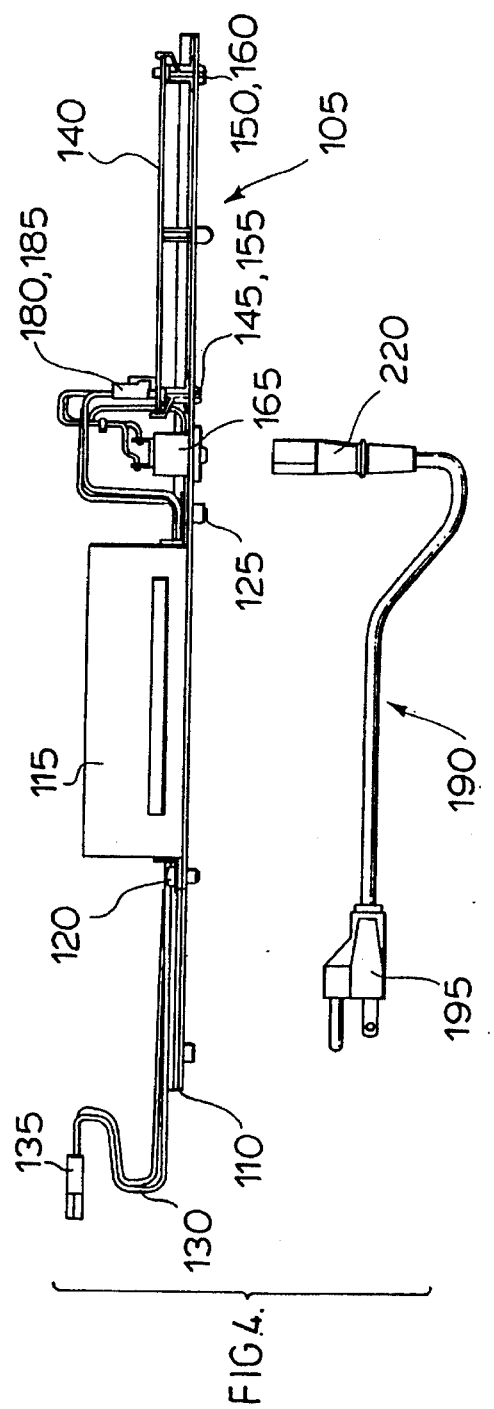
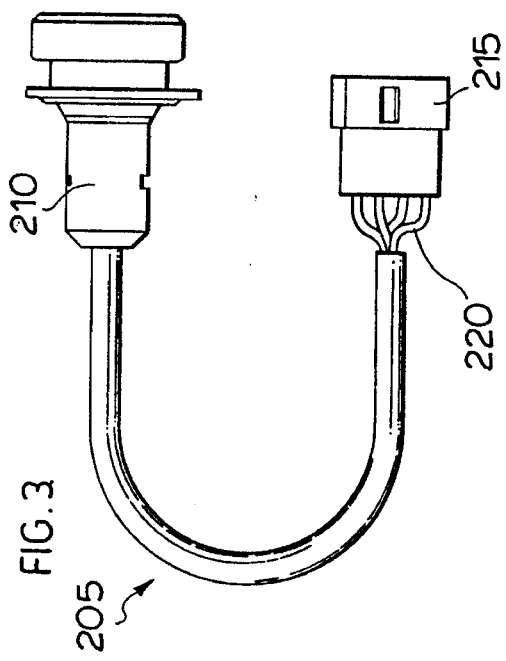

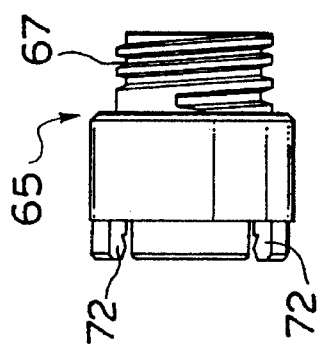
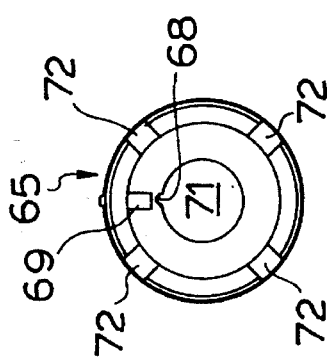
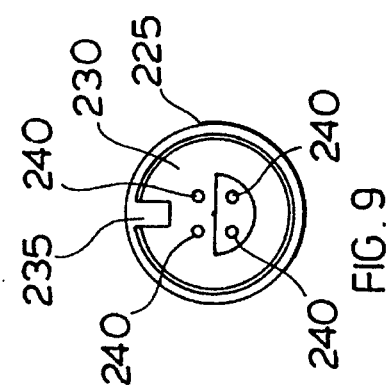
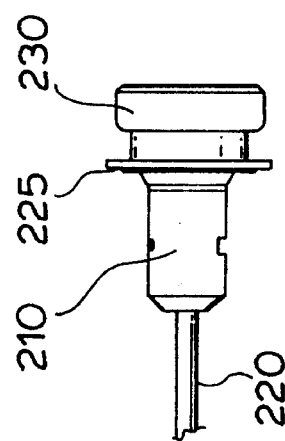
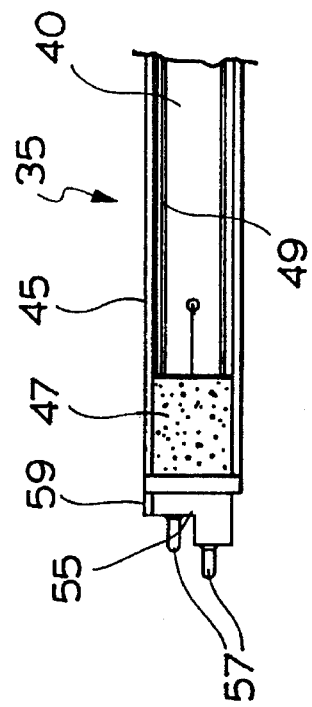
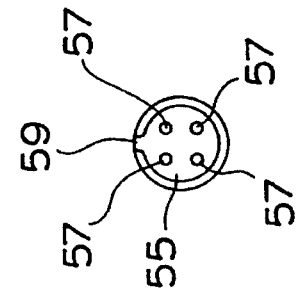
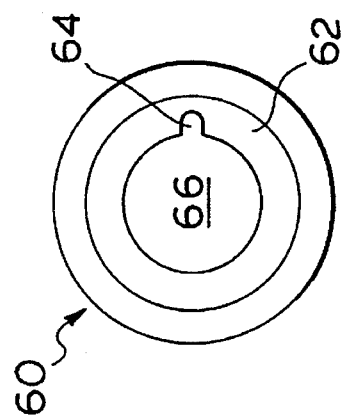

FLUID DISINFECTION SYSTEM

BACKGROUND OF THE INVENTION

1. Field of the Invention

The present invention relates to a fluid disinfection unit. More particularly, the present invention relates to a modular water disinfection unit which employs ultraviolet radiation to inactivate microorganisms.

2. Description of the Prior Art

It is known that irradiation of a fluid, such as water, with ultraviolet light will disinfect the water through inactivation of microorganisms therein, provided the irradiation intensity and exposure duration are above a minimum "dose" level (often measured in units of microwatt seconds per square centimeter). Ultraviolet water disinfection units, such as those commercially available from Trojan Technologies Inc. under the tradename UV600, employ this principle to disinfect water for human consumption. Generally, water to be disinfected passes through a pressurized stainless steel cylinder which is flooded with ultraviolet radiation. Large scale municipal wastewater treatment equipment, such as that commercially available from Trojan Technologies Inc. under the tradename UV3000, employ this same principle to disinfect treated wastewater. Specifically, ultraviolet radiation emitting lamps are submerged in an open channel wherein the wastewater is exposed to radiation as it flows past the lamps. For further disclosure of fluid purification systems employing ultraviolet radiation see U.S. Pat. Nos. 4,482,809, 4,872,980 and 5,006,244 and copending U.S. patent application Ser. No. 08/026,572, the contents of each of which is incorporated herein by reference.

Residential ultraviolet water disinfection products can vary in exact construction from one manufacturer to the next while still achieving similar operational characteristics. The major components that are common to most or all residential ultraviolet water disinfection units include: an ultraviolet radiation lamp; a water cylinder (often constructed of stainless steel because of the inherent resistance to corrosion and ultraviolet radiation); fastening fixtures/devices to secure the lamp in the cylinder; sealing devices to prevent water leakage from the entry point(s) of the lamp; a lamp ballast (power supply and starter); and power cords to connect the lamp to the ballast and to connect the ballast to external power. In addition, many residential ultraviolet disinfection products also contain the following components: a quartz sleeve with a larger diameter than the ultraviolet radiation lamp, which encases and thus protects the ultraviolet radiation lamp; an electrical circuit or printed circuit board which is capable of monitoring the lamp operation, monitoring signal(s) from an ultraviolet radiation intensity sensor built into the cylinder, and/or triggering alarms within the residence if the monitored signals indicate incorrect operation.

A problem associated with prior art residential ultraviolet water disinfection units is the difficulty in interchanging, servicing, and replacing electrical component parts. Residential ultraviolet water disinfection units presently available use soldered or crimped electrical connections between the lamp connector, ballast, electrical circuits (or printed circuit boards) and the power cord. Removal or replacement of defective, damaged or worn out electrical components requires special tools such as soldering and crimping equipment and, in many cases, may require wiring preparation and installation that cannot reliably be undertaken by the end user.

Another problem that occurs intermittently with certain residential ultraviolet water disinfection units involves interference in the light (radiation) path between the lamp and ultraviolet sensor by wires on the outside of the lamp. In order to clearly understand this problem, further background explanation is required.

Commercially, the most popular ultraviolet radiation lamp constructions for use in North American residential water disinfection units are the preheat and instant start styles that have all external electrical connections moved to one end of the lamp. With all electrical connections at one end, the user only needs to attach one connector to power the lamp. The single-ended preheat construction has a four-wire connection at one end, while the instant start lamp has a two-wire connection at one end. A powered filament is required at each end for the lamp are, so one or two Teflon-insulated wires are run along the outside of the lamp to connect the lamp end that has the external electrical connections to the filament at the other end. Residential water disinfection units that feature ultraviolet-radiation sensitive sensors to monitor the radiation intensity level rely on there being an optical path between the lamp and the sensor that is unblocked, save for the water that is being disinfected. If the angular orientation of Teflon-insulated wires is not specifically controlled by the design of the lamp, cylinder and securing fixtures, the wire insulation may block a portion of the ultraviolet radiation measured by the sensor, and cause a low (inaccurate) intensity feedback signal from the sensor. A low intensity feedback signal may prompt the end user to seek or perform unnecessary servicing.

Another problem that can exist with residential ultraviolet disinfection is that of "shadowing" caused by the lamp (or lamp and sleeve) support fixtures. When ultraviolet radiation lamps that have all external electrical connections at one end are employed for disinfection in a closed and pressurized cylinder, it is cost-effective to have the lamp enter the cylinder or one end only and to employ a support clip or fixture inside the other end of the cylinder to support the end of the lamp that does not have the external electrical connections (typically a closed end). The support clip or fixture must provide mechanical support and center positioning of the lamp or, if present, the protective sleeve surrounding the lamp. The support clip or fixture must provide centering for insertion of a replaced lamp or, if present, the protective sleeve so that an unskilled individual who is inserting the lamp from the one open end of the reactor chamber (cylinder) can simply push the lamp into place and have it automatically locate a centered position, regardless of the orientation of the reactor chamber or whether the lamp axis is ideally parallel to the reactor chamber axis when the lamp end reaches the fixture. The problem that exists with such a support fixture is that in order for it to be cost-effective and yet provide all of the mechanical features named, it can be bulky and can tend to block direct ultraviolet radiation from reaching the interior surfaces in the closed end of the cylinder. This blocking effect is commonly referred to as "shadowing" and is undesirable because any area under shadow will receive less of the ultraviolet radiation intended for disinfection of the water.

It would be desirable to have a fluid disinfection unit which, from the perspective of the end user, is free of relatively complicated electrical connections and/or exhibits minimal or no "shadowing".

SUMMARY OF THE INVENTION

It is an objective of the present invention to provide a fluid disinfection unit which obviates or mitigates at least one of the above-identified disadvantages associated with the prior art.

Accordingly, in one of its aspects, the present invention provides a fluid disinfection unit comprising a fluid treatment housing, an electrical supply module and electrical connection means connecting the fluid treatment housing and the electrical supply module;

the fluid treatment housing comprising a fluid inlet and a fluid outlet in communication with a reaction chamber, an ultraviolet radiation lamp disposed in the reaction chamber and having a first electrical connection receiving means at a first end thereof and a second end thereof being closed, the second end of the ultraviolet radiation lamp being received and held in place by fixture means;

the electrical supply module comprising ballast means and a second electrical connection receiving means; and the electrical connection means comprising lamp receptacle connector means at one end thereof for removable connection to the ultraviolet radiation lamp and electrical connection receiving means for connection to the electrical supply module.

As will be described hereinbelow, an aspect of the invention relates to the provision of a fluid disinfection unit in which the electrical wiring between the fluid treatment housing and the electrical supply module may be quick connected. By the term "quick connected", it is meant that electrical connection of the components may be effected quickly and readily by the end-user using a simple mechanical action such as push and turn, turn or push. The quick connection may be achieved using keyed male/female connectors in the fluid treatment housing, the electrical supply module and the electrical connection means.

Thus, the invention relates to a modular approach to the design of fluid disinfection units, particularly residential water disinfection units, that employ ultraviolet radiation lamps, preferably with protective quartz sleeves situated within a stainless steel cylinders, to disinfect water for potable use. The invention utilizes polarizing keys to control and optimize the angular orientation of the ultraviolet radiation lamp. In a preferred embodiment, the invention comprises the use as a fixture means in the fluid treatment housing of a novel helical spring to provide support, centering and cushioning of the ultraviolet radiation lamp within the housing.

BRIEF DESCRIPTION OF THE DRAWINGS

Embodiments of the present invention will be described with reference to the accompanying drawings, in which:

FIG. 3 illustrates a side elevation of the electrical connection means of a fluid disinfection unit in accordance with a first embodiment of the present invention;

FIG. 4 is an elevation of the electrical supply module illustrated in FIG. 2;

FIG. 8 illustrates a side elevation of a lamp receptacle connector;

FIG. 9 illustrates a front elevation of the lamp receptacle connector depicted in FIG. 8;

FIG. 10 illustrates a side elevation of a sleeve bolt for receiving the lamp receptacle connector depicted in FIGS. 8 and 9;

FIG. 11 illustrates a front elevation of the sleeve bolt depicted in FIG. 10;

FIG. 12 illustrates a front elevation of a portion of one end of the fluid treatment housing;

FIG. 13 illustrates a front elevation of an ultraviolet radiation lamp suitable for use in the present fluid disinfection unit;

FIG. 14 illustrates a side elevation of the ultraviolet radiation lamp depicted in FIG. 13.

In the Figures, like reference numerals from one Figure to the next refer to like parts.

DETAILED DESCRIPTION OF THE PREFERRED EMBODIMENTS

Figure 1:
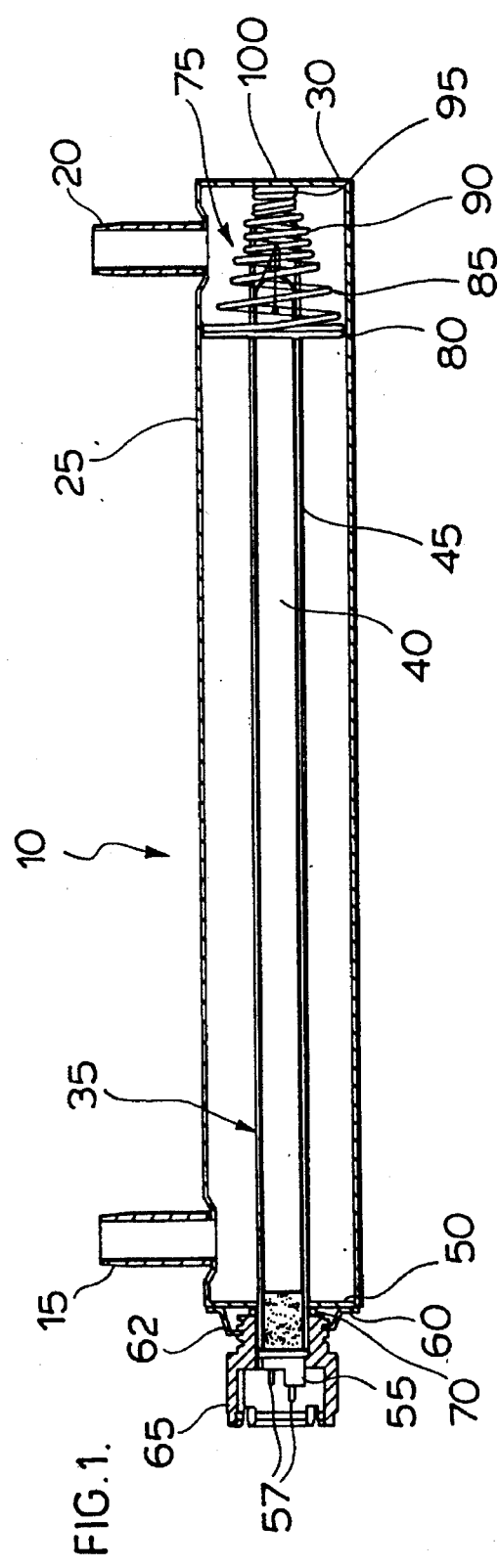
FIG. 1 illustrates a cross-sectional view of the fluid treatment housing of a fluid disinfection unit in accordance with a first embodiment of the present invention.

With reference to FIG. 1, there is illustrated a fluid treatment housing 10 comprising an inlet 15 and an outlet 20 in sealed communication with a reaction chamber 25. Reaction chamber 25 is sealed at one end thereof by an end cap 30. Disposed with reaction chamber 25 is an ultraviolet radiation lamp 35 comprising a lamp unit 40 and a protective quartz sleeve 45 surrounding lamp unit 40. Lamp unit 40, in normal operation, emits ultraviolet radiation having a wavelength of about 253.7 nanometers. Lamp 35 is commercially available from Voltarc (Connecticut) and Light Sources (Connecticut). The other end of reaction chamber 25 comprises a disk 50 sealingly engaged at its edges to reaction chamber 25.

As illustrated in FIG. 1, lamp 35 is closed at its end adjacent to end cap 30. The other end of lamp 35 comprises an electrical connection block 55 which protrudes from disk 50 of reaction chamber 25. A press nut 60 is suitably affixed to disk 50 (e.g. by spot welding) of reaction chamber 25. A sleeve bolt 65 is then threaded in press nut 60 to compress an O-ring 70 provided around quartz sleeve 45 into sealing engagement with both lamp 35 and disk 50. The closed end of lamp 35 is disposed in a helical spring 75 which abuts end cap 30.

Figure 7:
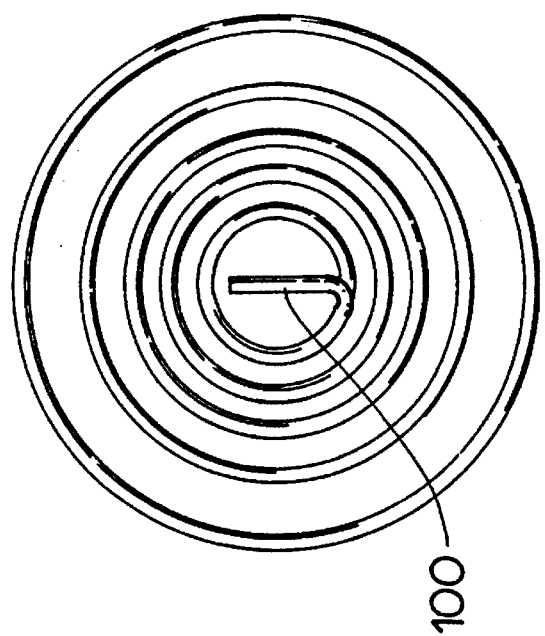
FIG. 7 illustrates a front elevation of a portion of the ultraviolet radiation lamp fixture means depicted in FIG. 6.
Figure 6:
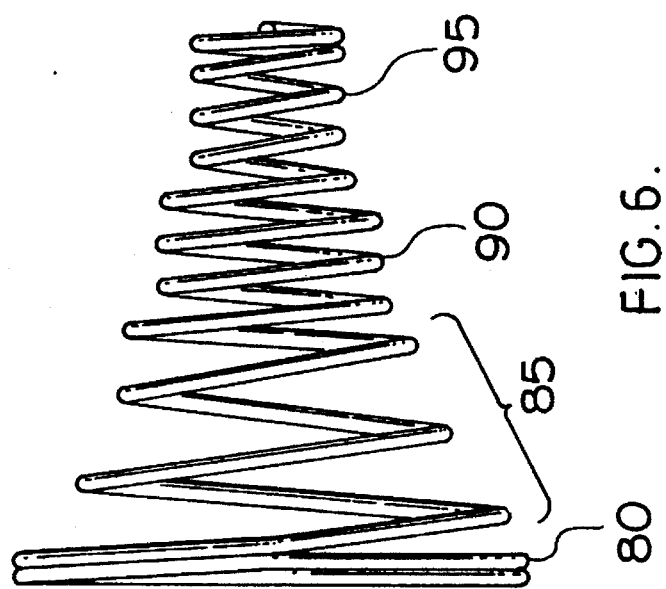
FIG. 6 illustrates a side elevation of an ultraviolet radiation lamp fixture means.

With further reference to FIG. 1 and reference to FIGS. 6 and 7, helical spring 75 is configured as follows. Helical spring 75 is composed of five main sections: (i) a first section 80 having a relatively large diameter which is sized to be slightly smaller than the inside diameter of reactor chamber 25; (ii) a second section 85 of decreasing diameter; (iii) a third section 90 of constant diameter windings that is sized to have an inside winding diameter slightly larger than the outer diameter of lamp 35; (iv) a fourth section 95 of constant diameter windings that is sized to have an inside diameter winding smaller than the outer diameter of lamp 35; and (v) a bent leg 100 that passes through the central axis of spring 75.

In use spring 75 serves as a centering and support fixture for the closed end of lamp 35. The function of spring 75 will be described with reference to FIGS. 6 and 7, and the portion of FIG. 1 which illustrates lamp 35 correctly seated in spring 75 within reactor chamber 25. The above-described sections of spring 75 perform the following functions: (i) first section 80 acts to center spring 75 within reactor chamber 25; (ii) second section 85, in combination with first section 80, serves to form a cone which directs an inserted closed end of lamp 35 toward the center of reactor chamber 25; (iii) third section 90 serves to cradle and support the inserted closed end of lamp 35 thereby protecting the fragile lamp end from physical shock imparted on the reactor chamber; (iv) fourth section 95 serves to provide additional centering of lamp 35 and acts, in and of itself, as a spring which is slightly compressed by inserted lamp 35 thereby minimizing or inhibiting movement of lamp 35 relative to spring 75; and (v) bent leg 100 serves as a point for affixation of spring 75 to end cap 30 of reactor chamber 25 thereby permanently securing spring 75 in place.

There are a number of advantages associated with helical spring 75. Spring 75 meets the requirements for centering, support, securing and protection of lamp 35 within reaction chamber 25. Spring 75 may be manufactured from a single piece of helically wound wire, rather than bulky sheet or structural metal, so it blocks less radiation and thus dramatically reduces shadowing effects within reactor chamber 25. Spring 75 can be manufactured readily and inexpensively compared to other types of fixtures, through the use of conventional spring-making equipment.

Figure 2:
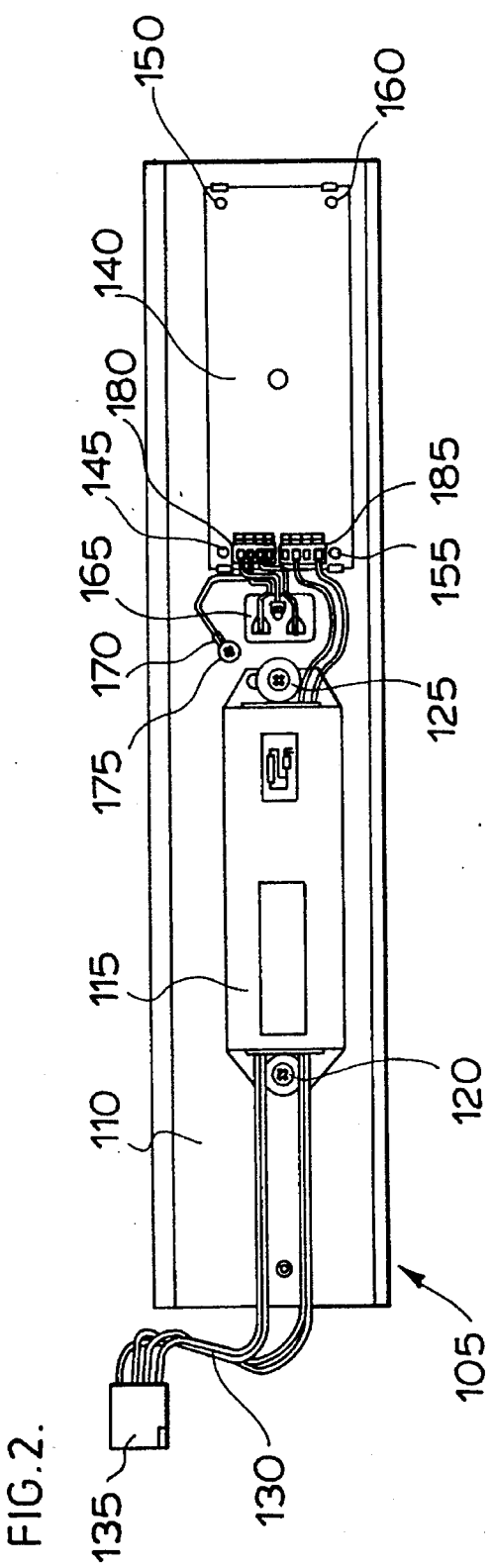
FIG. 2 illustrates a top plan view of the electrical supply module of a fluid disinfection unit in accordance with a first embodiment of the present invention.

With reference to FIGS. 2 and 4, there is illustrated an electrical supply module 105 comprising a sub-assembly base 110. A power supply ballast 115 is secured to sub-assembly base 110 by screws 120,125. Emerging from one end of power supply ballast 115 is a series of wires 130 terminating in a first electrical connector 135. A printed circuit board 140 is secured to sub-assembly base 110 by insulating polymer standoffs 145,150,155,160. The function of printed circuit board 140 is to monitor power consumption by power supply ballast 115 or radiation intensity output from lamp 35 and to activate, if necessary, an alarm should a failure condition exist in either of these parameters. A power supply harness 165 is secured to sub-assembly base 110 by any suitable insulating means and has emerging therefrom ground wire 170 which is secured to sub-assembly base 110 by a screw 175. Power supply harness 165 is connected to printed circuit board 140 via a locking four-pin connector 180. Power supply ballast 115 is connected to printed circuit board 140 via a locking four-pin connector 185. Power from a main supply (not shown) reaches electrical supply module through a power supply cord 190 having a first plug 195 at one end thereof for connection to an electrical wall socket and a second plug 200 at the other end thereof for connection to power supply harness 165. Power from the main supply is monitored by printed circuit board 140 and is re-directed to power supply ballast 115. Electrical supply module 105 may be enclosed by a suitable cover (not shown) which is removable and attaches to sub-assembly base 110.

Electrical supply module 105 is connected to fluid treatment housing 10 via an electrical connector 205. With reference to FIG. 3, at one end of electrical connector 205, there is provided a lamp receptacle connecter 210 for engagement of sleeve bolt 65 (described in more detail hereinafter) of fluid treatment housing 10. At the other end of electrical connector 205, there is provided a female connector 215 for engagement of first electrical connector 135. A series of wires 220 connect lamp receptacle connector 210 and female connector 215.

Figure 5:
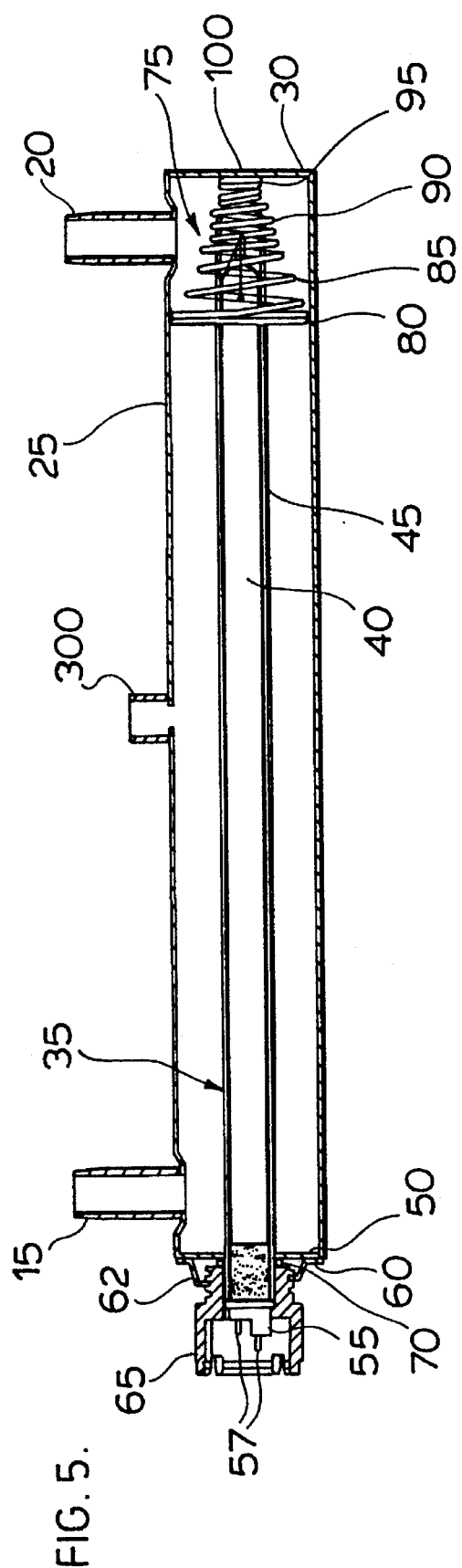
FIG. 5 illustrates a cross-sectional view of the fluid treatment housing of a fluid disinfection unit in accordance with a second embodiment of the present invention.

With reference to FIG. 5, there is illustrated an alternate embodiment of the fluid treatment housing. Specifically, in this embodiment reaction chamber 25 is modified to include a sensor port 300 which accommodates an ultraviolet radiation sensor (not shown) allowing for monitoring of the level of radiation to which the fluid being treated is exposed. This in turn allows for the ability to more precisely determine when lamp 35 is not functioning properly. Ultraviolet radiation sensors are known in the art and the choice thereof for use in the present invention is not particularly restricted. In a particularly preferred embodiment, the ultraviolet sensor is of the type disclosed in copending U.S. patent application Ser. No. 08/181,205, filed on even dated herewith in the name of the assignee named in this patent application.

With reference to FIGS. 13 and 14, lamp 35 will be described in more detail. Specifically, lamp unit 40 comprises a ceramic end piece 47 and lamp wires 49. Electrical connection block 55 of lamp 35 comprises four connection pins 57 and a first key 59.

With reference to FIG. 12, press nut 60 comprises a raised portion 62 (see FIG. 1 also). Raised portion 62 comprises a threading notch 64 and an aperture 66 for receiving sleeve bolt 65.

With reference to FIGS. 10 and 11, sleeve bolt 65 comprises a threaded portion 67, a first keyway 68, a second key 69 and an aperture 71 for receiving lamp 35. Sleeve bolt 65 also comprises four notches 72 for engagement of a suitable tool for facilitating installation and removal of sleeve bolt 65.

Lamp 35 may be installed within reactor chamber 25 as follows. Initially, O-ring 70 is placed on lamp 35 at approximately the location of ceramic end piece 47, after which sleeve bolt is placed thereover in a manner such that first key 59 of lamp 35 engages first keyway 68 of sleeve bolt 65. The closed end of lamp 35 is then inserted in reaction chamber 25. When the closed end of lamp 35 approaches end cap 30, spring 75 serves to center and position lamp 35. At this point threaded portion 67 of sleeve bolt 65 may be engaged with raised portion 62 of press nut 60. As sleeve bolt 65 is tightened, O-ring 70 is compressed into sealing engagement with lamp 35 and disk 50.

With reference to FIGS. 8 and 9, lamp receptacle connector 210 and connection of it to sleeve bolt 65 will be described in more detail. Specifically, lamp receptacle connector 210 comprises a cover 225 and a receptacle 230. Receptacle 230 comprises a second keyway 235 to receive second key 69 of sleeve bolt 65 and four pin sockets 240 for receiving complementary connection pins 57 of electrical connection block 55. Indeed, the design lamp receptacle connector 210 and lamp 35 is such that engagement thereof can be achieved only by engagement of: (i) pin sockets 240 and connection pins 57, and (ii) second key 69 and second keyway 235.

The modular design of the present fluid disinfection unit allows for rapid replacement of those electrical components known to have failed or for rapid replacement of all electrical components (i.e. electrical supply module 105 in its entirety) when a diagnosis is either inconclusive or not feasible. Any of the electrical components described hereinabove can be removed and inspected, serviced, and/or replaced easily and quickly with no specialized tool requirement. Depending on the exact design, conventional tools may be required if the power supply ballast 115, power supply harness 165 and/or entire electrical supply module 105 are to be removed/replaced. The modular design approach also makes it possible for a service personnel to diagnose a problem in a single electrical component within an ultraviolet residential water disinfection unit by simply and rapidly changing out parts until the desired operation or performance is observed.

An advantage of the design described hereinabove is that all major components that can influence the angular orientation of the ultraviolet radiation lamp, including the lamp itself, are keyed or tightened together. Through selection of the angular position at which the threading notch 64 of the press nut 60 is affixed to the reactor chamber 25, the final angular position of the lamp wires 49 relative to the sensor port 300 can be controlled.

It should be understood that, while exemplary embodiments of the present invention have been described herein, the present invention is not limited to these exemplary embodiments and that variations and other alternatives may occur to those of skill in the an without departing from the intended scope of the invention as defined by the attached claims.

What is claimed is:

1. A fluid disinfection unit comprising (i) a fluid treatment housing, (ii) an electrical supply module, and (iii) electrical connection means connecting the fluid treatment housing and the electrical supply module;
   (i) the fluid treatment housing comprising a fluid inlet and a fluid outlet in communication with a reaction chamber, an ultraviolet radiation lamp disposed in the reaction chamber and having a first electrical connection means at a first end of said lamp, said lamp being surrounded by a sleeve, an end of the sleeve distal the first end of said lamp having a closed end and being received and held in place by a spring having a first diameter less than diameter of said sleeve, and a second diameter greater than a diameter of said sleeve;
   (ii) the electrical supply module comprising ballast means and a second electrical connection means; and
   (iii) the electrical connection means comprising lamp connector means for removable connection to said first electrical connection means, and ballast connector means for connection to said second electrical connection means.

2. The fluid disinfection unit defined in claim 1, wherein said spring is a helical spring.

3. The fluid disinfection unit defined in claim 2, wherein said helical spring is tapered.

4. The fluid disinfection unit defined in claim 3, wherein said spring comprises a first, leading portion having a diameter slightly less than that of the reaction chamber.

5. The fluid disinfection unit defined in claim 4, wherein said spring comprises a second portion after the first, leading portion, the second portion comprising a decreasing diameter.

6. The fluid disinfection unit defined in claim 5, wherein said spring comprises a third portion after the second portion, the third portion having said second diameter.

7. The fluid disinfection unit defined in claim 6, wherein said spring comprises a fourth portion after the third portion, the fourth portion having said first diameter.

8. The fluid disinfection unit defined in claim 7, wherein said spring comprises a fifth portion after the fourth portion, the fifth portion comprising affixation means for securing the spring to the reaction chamber.

9. The fluid disinfection unit defined in claim 1, wherein said reaction chamber further comprises ultraviolet radiation sensor means.

10. The fluid disinfection unit defined in claim 1, wherein said ultraviolet radiation lamp and said lamp receptacle connector means are keyed to one another.

11. A fluid disinfection unit comprising:
    a chamber having a fluid inlet, a fluid outlet, and a removable end and an opposite end;
    a radiation unit disposed in said chamber and having a radiation lamp surrounded by a sleeve;
    an electrical connector coupled to one end of said sleeve and disposed at said removable end of the chamber; and
    a spring having a first diameter less than a diameter of said sleeve, and a second diameter greater than a diameter of said sleeve, said spring disposed at the opposite end of said chamber for receiving and cushioning a second end of said sleeve.

12. A unit according to claim 11, wherein said spring is non-removable from said chamber.

13. A unit according to claim 12, wherein said spring is coupled to the opposite end of said chamber.

14. A unit according to claim 11, wherein said spring comprises a helical spring.

15. A unit according to claim 14, wherein said second diameter is substantially the same as an inside diameter of said chamber.

16. A unit according to claim 11, wherein the opposite end of said chamber is permanently sealed.

17. A fluid disinfection unit comprising (i) a fluid treatment housing, (ii) an electrical supply module, and (iii) electrical connection means connecting the fluid treatment housing and the electrical supply module:
    (i) the fluid treatment housing comprising a fluid inlet and a fluid outlet in communication with a reaction chamber, an ultraviolet radiation lamp disposed in the reaction chamber and having a first electrical connection means at a first end of said lamp, the second end of said lamp being received and held in place by a fixture means;
    (ii) the electrical supply module comprising ballast means and a second electrical connection means;
    (iii) the electrical connection means comprising lamp connector means for removable connection to said first electrical connection means, and ballast connector means for connection to said second electrical connection means; and
    (iv) said fixture means comprising a tapered helical spring having a first portion with a diameter slightly less than that of the reaction chamber, a second portion having a decreasing diameter, and a third portion having a substantially constant diameter which is slightly larger than that of said lamp.

18. A unit according to claim 17, wherein said ultraviolet radiation lamp includes a sleeve surrounding an ultraviolet radiation bulb, an end of said sleeve distal the first end of said lamp having a closed end and being received and held in place by said fixture means.

19. A unit according to claim 17, wherein said helical spring is coupled to an end of said fluid treatment housing.

20. A unit according to claim 17, further comprising an ultraviolet radiation sensor coupled to said fluid treatment housing, for sensing radiation output by said ultraviolet radiation lamp.

* * * * *